United States Patent [19]

Pedersen

[11] 4,165,299

[45] Aug. 21, 1979

[54] PREPARATION OF A SINGLE PHASE VANADIUM (IV) BIS (METAPHOSPHATE) OXIDATION CATALYST WITH AN IMPROVED SURFACE AREA

[75] Inventor: S. Erik Pedersen, Mentor, Ohio

[73] Assignee: Atlantic Richfield Company, Los Angeles, Calif.

[21] Appl. No.: 908,869

[22] Filed: May 23, 1978

[51] Int. Cl.$^2$ .................... B01J 27/14; C01B 15/16; B01J 27/02
[52] U.S. Cl. .................... 252/435; 252/437; 423/314; 252/440
[58] Field of Search .................... 252/435, 437, 440; 423/314

[56] References Cited

U.S. PATENT DOCUMENTS

| | | | |
|---|---|---|---|
| 3,031,508 | 4/1962 | Etherington et al. | 252/437 X |
| 3,293,268 | 12/1966 | Bergman et al. | 252/437 X |
| 3,977,998 | 8/1976 | Freerks et al. | 252/435 |
| 4,043,943 | 8/1977 | Schneider | 252/435 X |
| 4,092,269 | 5/1978 | Mount et al. | 252/437 X |

OTHER PUBLICATIONS

Journal of Catalyst 34, 345–355 (1974) Nakamura et al.

*Primary Examiner*—Delbert E. Gantz
*Assistant Examiner*—William G. Wright
*Attorney, Agent, or Firm*—Delbert E. McCaslin

[57] ABSTRACT

A method for the preparation of a single phase vanadium(IV)bis(metaphosphate), VO(PO$_3$)$_2$, catalyst having an improved surface area and useful for the vapor phase oxidation of linear C$_4$ unsaturated olefins, such as the n-butenes, to prepare maleic anhydride.

4 Claims, No Drawings

PREPARATION OF A SINGLE PHASE VANADIUM (IV) BIS (METAPHOSPHATE) OXIDATION CATALYST WITH AN IMPROVED SURFACE AREA

RELATED APPLICATIONS

This application is related to co-pending S. E. Pedersen application Ser. No. 889,785, filed Mar. 24, 1978, entitled PREPARATION OF MALEIC ANHYDRIDE USING A VANADIUM(IV)BIS(METAPHOSPHATE) CATALYST which application discloses certain aspects of the present invention.

FIELD OF THE INVENTION

This invention is directed to a method for the preparation of an improved vanadium(IV)bis(metaphosphate) oxidation catalyst. More particularly, it relates to a unique method for the preparation of the single phase vanadium(IV)bis(metaphosphate) catalyst to provide greater intrinsic surface area and thus improved activity and selectivity for use in the production of maleic anhydride from unsaturated hydrocarbon feed.

BACKGROUND OF THE INVENTION

In the above co-pending application of S. E. Pedersen, Ser. No. 889,785, which application is incorporated herein by reference, there is disclosed and claimed a method for the preparation of maleic anhydride by oxidizing an unsaturated aliphatic hydrocarbon in the vapor phase at temperatures of from about 300° C. to 600° C. and pressures of from about ambient to 1000 psig with oxygen or an oxygen-containing gas, such as air, in the presence of a single phase vanadium(IV)bis(metaphosphate) catalyst. This catalyst which may be prepared by the methods disclosed in the above noted co-pending Pedersen application or in an article by Bruce C. Tofield et al, J.A.C.S., Dalton Transactions, Part II, 1975, pp. 1806–1810 and G. Ladwig, Z. Chem., 1968, Vol. 8, p. 307, which after activation or conditioning, is a good oxidation catalyst for unsaturated aliphatic hydrocarbons to produce maleic anhydride, suffers from a disadvantage in that it has an intrinsic surface area of only 0.30 to 0.50 m$^2$/gm. Such limited intrinsic surface area is generally undesirable because the activity of the oxides of vanadium and phosphorus are directly related to the intrinsic surface area, particularly when employed as oxidation catalysts to prepare maleic anhydride.

SUMMARY OF THE INVENTION

According to the present invention there is provided a novel method for preparing a single phase vanadium-(IV)bis(metaphosphate), VO(PO$_3$)$_2$, catalyst, which method substantially increases the intrinsic surface area of the compound and improves the catalytic activity and selectivity for an air or oxygen partial oxidation of an unsaturated aliphatic hydrocarbon selected from 1-butene, 2-butene, and 1,3-butadiene or mixtures thereof at temperatures of from about 300° C. to 600° C. by contacting said hydrocarbon and air or oxygen with the vanadium(IV)bis()metaphosphate), at contact times of from about 0.5 to 10 seconds of reactant feed over the compound, prepared by the instant method.

It is a primary object of this invention to provide a method for the preparation of a single phase vanadium-(IV)bis(metaphosphate) useful as an oxidation catalyst to produce maleic anhydride and having a significantly improved intrinsic surface area.

It is another object of this invention to provide a novel type single phase vanadium(IV)bis(metaphosphate) catalyst having intrinsic surface area of from about 1.5 to 5.0 m$^2$/gm. which provides yields of and selectivities to maleic anhydride which are higher than heretofore obtained by the oxidation of unsaturated aliphatic hydrocarbons.

These and other objects and advantages of this invention will become apparent from the description of the invention which follows and from the claims.

DESCRIPTION OF THE INVENTION

In accordance with the present invention, a single phase vanadium(IV)bis(metaphosphate), VO(PO$_3$)$_2$ compound is prepared by a novel method which improves the intrinsic surface area significantly as compared to known VO(PO$_3$)$_2$ catalyst preparation methods described in the aforementioned S. E. Pedersen co-pending application Ser. No. 889,785, filed Mar. 24, 1978. The catalyst may be employed as an oxidation catalyst to produce maleic anhydride from 1-butene, 2-butene, and 1,3-butadiene or mixtures thereof under the activation and oxidation reaction conditions set forth herein and in the above-mentioned S. E. Pedersen application.

The instant method for preparation of the vanadium-(IV)bis(metaphosphate) oxidation catalyst compound having an intrinsic surface area of from about 1.5 to 5.0 m$^2$/gm. involves a solid state thermal reaction between vanadyl sulfate (VOSO$_4$) and phosphorus pentoxide with the liberation of gases according to the following postulated equation:

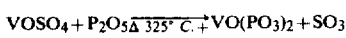

$$VOSO_4 + P_2O_5 \xrightarrow{\Delta\ 325°\ C.} VO(PO_3)_2 + SO_3$$

The catalyst possesses a vanadium oxygen double bond and has a highly ordered structure. Stoichiometric amounts of the vanadyl sulfate and phosphorus pentoxide are generally employed in preparing the VO(PO$_3$)$_2$ compound but excess amounts of either compound may also be used and the excess residue removed, by water washing, after reaction to form the catalyst precursor. The reaction will proceed at temperatures of at least 325° C. and temperatures as high as 475° C. or higher may be employed to liberate the reaction gases. It is generally preferred to carry out the reaction at a temperature of about 400° C. to obtain a convenient rate of reaction.

After preparation and water washing, the VO(PO$_3$)$_2$ compound is generally dried at 120° C., calcined in air at temperatures between about 450° C. and 500° C. or higher for at least two hours, then broken up and sieved to the appropriate Tyler Standard Sieve mesh size, usually for fixed bed reactor use. The resulting VO(-PO$_3$)$_2$ compound (catalyst precursor) which has a surface area of approximately 1.5 to 5.0 m$^2$/gm. requires a period of activation or conditioning for use in oxidizing the above indicated unsaturated aliphatic hydrocarbons. For the activation or conditioning the catalyst precursor is subjected to temperatures which are at or above the hydrocarbon oxidation reaction temperatures which are from about 300° C. to 600° C. preferably from 450° C. to 550° C., under a flow of from about 0.2 volume percent to about 2.0 volume percent preferably 0.5 to 1.5 volume percent in air of said hydrocarbon, or mixture of hydrocarbons, to be oxidized and at an apparent contact time of from about 1 to 10 seconds, preferably 4 to 8 seconds for an appropriate period, to enable the hydrocarbon conversion to reach 90 percent or more, with subsequent temperature and flow rate adjustments to desired oxidation reaction conditions. The length of time required for activation or conditioning of the catalyst precursor and to permit the catalyst performance to become stabilized depends on the temperature employed and contact time of the hydrocarbon-air mixture but generally will be from about 4 to 8 hours. Apparent contact time calculated in seconds is equal to the flow rate of the hydrocarbon-air feed mixture at cc/seconds, per cc of catalyst measured at ambient conditions. Once activated the $VO(PO_3)_2$ exhibits excellent performance as a catalyst for the oxidation of 1-butene, 2-butene and 1,3-butadiene, or mixtures thereof, to maleic anhydride for extended periods of time.

Although the $VO(PO_3)_2$ catalyst of this invention may be prepared in the appropriate mesh size and employed in the reactor as such, it may also be on inert support materials or carriers such as silica gel, alumina, silicon carbide, aluminosilicates and kieselguhr. The catalyst support, if employed, provides a surface for the catalyst and gives physical strength and stability to the catalyst material.

The following examples are provided to illustrate the invention in accordance with the principles of this invention but are not to be construed as limiting the invention in any way except as indicated by the appended claims.

In the Examples which follow that are directed to unsaturated hydrocarbon oxidation employing the instant catalyst, the reactions were run in a ⅜ inch inside diameter stainless steel U-tube reactor which was immersed in a fluidized sand bath for maintaining the temperature of reaction. The lower half of the U-tube reactor was filled with catalyst having an 8-16 mesh (Standard Sieve). The $VO(PO_3)_2$ (precursor) catalyst is activated or conditioned in a stream of air with 1 volume percent of unsaturated hydrocarbon at a desired temperature for several hours at an appropriate apparent contact time over the catalyst. Following activation the temperature is decreased to the desired oxidation reaction temperature and the flow of hydrocarbon-air mixture, with or without the addition of steam, adjusted to the desired apparent contact time of between about 1.5 to 4.0 seconds. The gaseous effluent oxidation reaction products from the reactor were passed through a series of water traps to absorb the maleic anhydride and other by-products such as trace amounts of acetic and acrylic acids; the maleic anhydride being converted to maleic acid in the aqueous solution. The gaseous effluent from the U-tube reactor was analyzed by InfraRed (I.R.) and gas chromatography to determine the concentration of carbon dioxide, carbon monoxide and any unconverted hydrocarbon. The aqueous solution containing the maleic acid was analyzed by gas chromatography and titrated to give the acid number, to determine maleic anhydride yield and selectivity. Percent conversion of hydrocarbon and percent selectivity to maleic anhydride are calculated in mole percent.

EXAMPLE 1

Catalyst Preparation

A vanadium(IV)bis(metaphosphate), $VO(PO_3)_2$, catalyst was prepared as follows: 140.5 g. (0.861 mole) of vanadyl sulfate ($VOSO_4$) and 119.42 g. (0.841 mole) of phosphorus pentoxide ($P_2O_5$) were thoroughly mixed in a nitrogen atmosphere and transferred to a furnace having a temperature of 100° C. The temperature of the furnace was increased at a rate of 1°/minute to a maximum of 400° C. and maintained for a period of three hours liberating the reaction gases. After cooling, the light blue product is thoroughly washed with water to remove any soluble residues. After drying at 120° C. the product was calcined in air at 500° C. for two hours to give a $VO(PO_3)_2$ catalyst (precursor) having an intrinsic surface area of approximately 2.4 $m^2$/gm. After calcination the vanadium(IV)bis(metaphosphate) catalyst precursor was broken up, 8-16 mesh size (Standard Sieve) for use, after activation or conditioning, in the oxidation of 1-butene, 2-butene and 1,3-butadiene to maleic anhydride.

EXAMPLE 2

Catalyst Preparation

A vanadium(IV)bis(metaphosphate), $VO(PO_3)_2$, catalyst for the oxidation of unsaturated aliphatic hydrocarbons was prepared as follows: 281 gm. of vanadyl sulfate ($VOSO_4$) and 238.84 gm. of phosphorus pentoxide ($P_2O_5$) were thoroughly mixed in a nitrogen atmosphere and transferred to a furnace having a temperature of 100° C. The temperature of the furnace was increased at a rate of 1°/minute to a maximum of 460° C. and maintained at that temperature for 3 hours liberating the reaction gases. After cooling, the light blue product was thoroughly washed with water to remove any soluble residues. After drying at 120° C., the product was calcined in air at 500° C. for two hours to give a $VO(PO_3)_2$ catalyst (precursor) having an intrinsic surface area of approximately 4.1 $m^2$/gm. After calcination the vanadium(IV)bis(metaphosphate) catalyst precursor was broken up to an 8-16 mesh size (Standard Sieve).

EXAMPLE 3

50 ml. of the vanadium(IV)bis(metaphosphate) of Example 1 was loaded into the lower half of the U-tube reactor which was immersed in a fluidized sand bath. The catalyst (precursor) was activated in a stream of air and 1 volume percent of 1,3-butadiene at 520° C. for four hours at an apparent contact time of 5.6 seconds during which period the activity of the catalyst increased to approximately 100 percent conversion of the 1,3-butadiene. Following conditioning of the catalyst the reaction temperature was decreased to the desired temperature and the apparent contact time adjusted to desired conditions. In a similar manner without reactivating or changing the catalyst, 2-butene and 1-butene were oxidized over the same catalyst. No steam was added to the reaction system. Results giving conversions and selectivities are tabulated in Table 1 below.

TABLE 1

| Run No. | Hydrocarbon | Contact Time (Sec.) | Temp. °C. | Mole % Conversion[1] | Mole % Selectivity to[2] Maleic Anhydride |
|---|---|---|---|---|---|
| 1 | 1,3-butadiene | 2.0 | 430 | 96 | 59.8 |
| 2 | 2-butene | 1.6 | 450 | 97.6 | 60.0 |

TABLE 1-continued

| Run No. | Hydrocarbon | Contact Time (Sec.) | Temp. °C. | Mole % Conversion[1] | Mole % Selectivity to[2] Maleic Anhydride |
|---|---|---|---|---|---|
| 3 | 1-butene | 1.6 | 450 | 100 | 60.3 |

[1]% Conversion of hydrocarbon analyzed by gas chromatograph and I.R.
[2]% Selectivity to maleic anhydride by gas chromatograph analysis and titration to give acid number.

EXAMPLE 4

A number of runs were made employing 50 ml. of the vanadium(IV)bis(metaphosphate) catalyst prepared in Example 2 and activated as in Example 3, for the oxidation of 1,3-butadiene and 1-butene with steam added to the reactant feed stream after adjustment to desired reaction temperature and apparent contact times for the feed stream. The results and reaction conditions are set forth in Table 2.

TABLE 2

| Run No. | Hydrocarbon | Steam Vol. % | Temp. °C. | Contact Time (sec.) | Mole % Conversion | Mole % Selectivity to Maleic Anhydride |
|---|---|---|---|---|---|---|
| 1 | 1,3-butadiene | 10 | 450 | 1.5 | 100 | 66.8 |
| 2 | 1,3-butadiene | 10 | 425 | 2.0 | 97 | 67.6 |
| 3 | 1,3-butadiene | 8 | 410 | 2.3 | 99 | 66.0 |
| 4 | 1-butene | 8 | 440 | 1.7 | 95 | 66.5 |
| 5 | 1-butene | 10 | 435 | 1.9 | 96 | 66.3 |
| 6 | 1-butene | 10 | 440 | 1.9 | 96 | 65.8 |

The higher intrinsic surface area $VO(PO_3)_2$ catalyst has proven to be an excellent catalyst for the oxidation of normal, unsaturated $C_4$ hydrocarbons to maleic anhydride. The higher surface area improved the activity of the catalyst which allows the process to be carried out under less severe reaction conditions. X-ray analysis (powder diffraction patterns) of the freshly prepared and activated $VO(PO_3)_2$ catalyst and a catalyst which had been on stream for 400 hours in the presence of from 8 to 10 percent steam were identical with no noticeable deterioration.

I claim:

1. A method for the preparation of a single phase vanadium(IV)bis(metaphosphate) oxidation catalyst for preparing maleic anhydride by oxidation of unsaturated aliphatic hydrocarbons, which catalyst has an intrinsic surface area of from about 1.5 to 5.0 $m^2/gm.$, which comprises the steps of:

forming a solid state mixture of vanadyl sulfate and phosphorus pentoxide;

introducing said mixture into a heating zone and maintaining said zone and mixture at a temperature of at least about 325° C. for a period sufficient for the liberation of gases and forming a vanadium phosphorus reaction product;

cooling the reaction product and washing with water to essentially remove any soluble residue;

drying the water washed product and calcining in air to obtain a single phase vanadium(IV)bis(metaphosphate) catalyst having an intrinsic surface area of from about 1.5 to 5.0 $m^2/gm.$ 2. A method according to claim 1 wherein at least stoichiometric amounts of vanadyl sulfate and phosphorus pentoxide are employed to form the solid state mixture.

3. A method according to claim 1 wherein the mixture of vanadyl sulfate and phosphorus pentoxide is reacted at a temperature of between about 400° C. and 460° C.

4. A method according to claim 1 wherein the reaction mixture is dried at a temperature of about 120° C. and calcined in air at a temperature of at least 450° C.

* * * * *